US012762810B1

(12) United States Patent
Durairaj et al.

(10) Patent No.: US 12,762,810 B1
(45) Date of Patent: Oct. 13, 2026

(54) AUGMENTED REALITY SYSTEM WITH DYNAMIC USER INTERFACE

(71) Applicant: United Services Automobile Association (USAA), San Antonio, TX (US)

(72) Inventors: Ravi Durairaj, San Antonio, TX (US); Ahmad Ali Shaik, Austin, TX (US); Andre Rene Buentello, San Antonio, TX (US); Jose L. Romero, Jr., San Antonio, TX (US); Will Kerns Maney, San Antonio, TX (US); Sydney Ann Conrad-Cook, Van Meter, IA (US); Paula Ann Whittington, Helotes, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 25 days.

(21) Appl. No.: 18/785,190

(22) Filed: Jul. 26, 2024

Related U.S. Application Data

(60) Provisional application No. 63/529,535, filed on Jul. 28, 2023.

(51) Int. Cl.

| | |
|---|---|
| ***G06T 19/00*** | (2011.01) |
| ***A61B 5/02*** | (2006.01) |
| ***G06F 3/01*** | (2006.01) |

(52) U.S. Cl.
CPC .............. *G06T 19/006* (2013.01); *A61B 5/02* (2013.01); *G06F 3/013* (2013.01)

(58) Field of Classification Search
None
See application file for complete search history.

(56) References Cited

U.S. PATENT DOCUMENTS

| | | | | |
|---|---|---|---|---|
| 10,242,501 | B1 * | 3/2019 | Pusch | H04N 19/43 |
| 10,558,740 | B1 * | 2/2020 | O'Malley | G06F 40/197 |
| 10,761,597 | B2 * | 9/2020 | Xu | G06F 3/011 |
| 2001/0034655 | A1 * | 10/2001 | Donlavage | G06Q 40/02 705/19 |
| 2018/0124242 | A1 * | 5/2018 | Zimmerman | H04M 3/5175 |
| 2020/0327743 | A1 * | 10/2020 | Cannarsa | G06Q 40/08 |
| 2021/0240452 | A1 * | 8/2021 | Schoppe | G06F 8/38 |

* cited by examiner

*Primary Examiner* — Jeffrey J Chow
(74) *Attorney, Agent, or Firm* — Fletcher Yoder, P.C.

(57) ABSTRACT

An augmented reality (AR) system includes a processing system with one or more processors and memory storing instructions executable by the processing system to cause the processing system to instruct display of information in a first format via a display of an AR device and monitor one or more physiological parameters of a user as the user views the information in the first format via the display of the AR device. The instructions are executable by the processing system to cause the processing system to, in response to the one or more physiological parameters of the user indicating a negative sentiment of the user as the user views the information in the first format via the display of the AR device, instruct display of the information in a second format via the display of the AR device.

20 Claims, 5 Drawing Sheets

AUGMENTED REALITY SYSTEM WITH DYNAMIC USER INTERFACE

CROSS-REFERENCE TO RELATED APPLICATION

This application claims priority to and the benefit of U.S. Provisional Application No. 63/529,535, entitled "AUGMENTED REALITY SYSTEM WITH DYNAMIC USER INTERFACE" and filed Jul. 28, 2023, which is incorporated by reference herein in its entirety for all purposes.

BACKGROUND

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statement are to be read in this light, and not as admission of prior art.

A consumer may periodically review and/or update insurance coverage. For example, the consumer may access an online account session to review information (e.g., parameters, such as deductibles, limits, and/or assets covered) about an insurance policy. In some cases, the consumer may provide inputs to perform various operations during the online account session, such as to update the parameters of the insurance policy, make a claim under the insurance policy, and so forth.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, an augmented reality (AR) system includes a processing system with one or more processors and memory storing instructions executable by the processing system to cause the processing system to instruct display of information in a first format via a display of an AR device and monitor one or more physiological parameters of a user as the user views the information in the first format via the display of the AR device. The instructions are executable by the processing system to cause the processing system to, in response to the one or more physiological parameters of the user indicating a negative sentiment of the user as the user views the information in the first format via the display of the AR device, instruct display of the information in a second format via the display of the AR device.

In one embodiment, an augmented reality (AR) system includes a processing system with one or more processors and memory storing instructions executable by the processing system to cause the processing system to receive a request from a user to initiate an AR experience via an AR device, access data relevant to the user from one or more databases, instruct display of information via a display of the AR device to present at least some of the data relevant to the user, and receive one or more inputs from the user as the user views the information via the display of the AR device. The instructions are executable by the processing system to cause the processing system to, based on the one or more inputs from the user, modify a format in which the information is displayed via the display of the AR device.

In one embodiment, a method of operating an augmented reality (AR) device includes instructing, using a processing system, display of information in a first format via a display of an AR device. The method also includes receiving, from one or more sensors and at the processing system, one or more physiological parameters of a user as the user views the information in the first format via the display of the AR device. The method also includes instructing, using the processing system, display of the information in a second format via the display of the AR device in response to the one or more physiological parameters of the user indicating a negative sentiment of the user as the user views the information in the first format via the display of the AR device.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
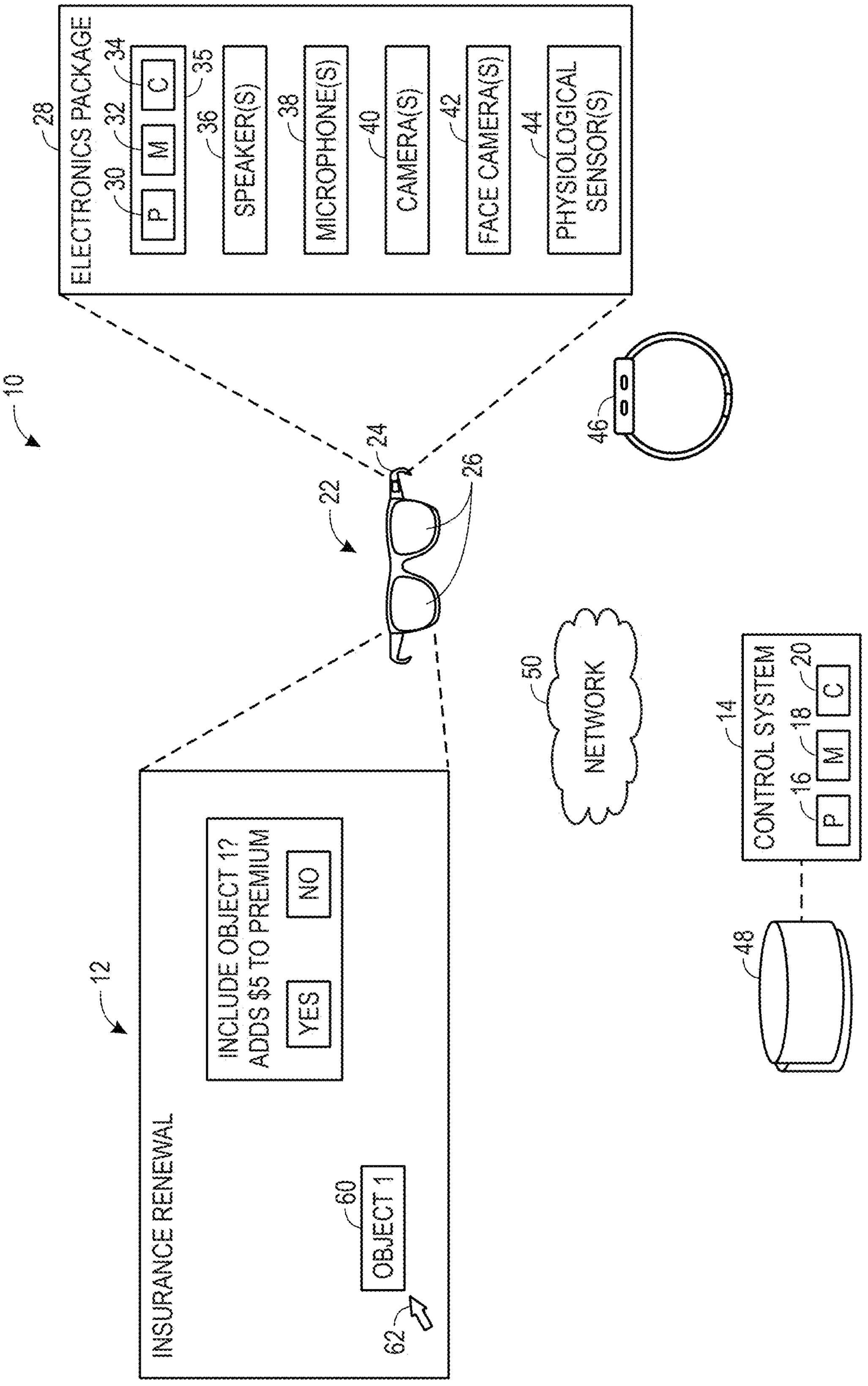
FIG. 1 is a schematic illustration of an augmented reality system that is configured to provide a dynamic user interface, in accordance with an embodiment of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

Present embodiments relate generally to an augmented reality (AR) system that provides a dynamic user interface to facilitate presentation of information to a user and/or to facilitate various operations by the user. For example, the AR system may include AR glasses with one or more displays (e.g., transparent displays; lenses). The AR system may instruct the AR glasses to display the information on the one or more displays, such that the user visualizes the information overlaid onto a real-world environment.

The AR system may also include various other devices. For example, the AR glasses may include one or more speakers to provide audio outputs. Additionally or alternatively, the AR glasses may include one or more sensors, such as one or microphones to detect audio inputs, one or more cameras to detect objects in an environment surrounding the AR glasses, one or more face cameras to detect eye gaze and/or a face of the user while the user wears the AR glasses, and/or one or more physiological sensors to detect physiological parameters of the user while the user wears the AR glasses. Additionally or alternatively, the AR system may include or be communicatively coupled to additional output devices and/or sensors that are physically separate (e.g., off-board) the AR glasses. For example, the AR system may include or be communicatively coupled to one or more physiological sensors in a wearable sensor associated with the user (e.g., the wearable sensor is configured to be held, carried, and/or worn by the user; integrated into a smart watch or a mobile phone of the user).

The AR system may utilize an insurance application (e.g., software application) to access insurance data from one or more databases and to present information that is relevant to an insurance policy via the AR glasses. For example, the AR system may utilize the insurance application to facilitate insurance renewal processes, insurance claim processes, and/or insurance application processes for the user via the AR glasses. Further, the AR system may utilize the insurance application to present the information via a dynamic user interface, wherein the AR system updates (e.g., changes) the dynamic user interface based on one or more inputs, including the audio inputs from the one or more microphones, imagery of the environment from the one or more cameras, imagery of the eye gaze and/or the face of the user from the one or more face cameras, and/or the physiological parameters of the user from the one or more physiological sensors. In this way, the AR system automatically and dynamically updates the dynamic user interface to present the information to the user in a format (e.g., content and/or layout; complex mode or simple mode; higher level or lower level; more options or fewer options) that is accessible to the user and/or comfortable for the user. Accordingly, the user may readily process and understand the information, as well as more easily provide inputs to perform insurance operations, such as to update the insurance policy and so forth.

With the foregoing in mind, FIG. 1 is a schematic illustration of an augmented reality (AR) system 10 that is configured to provide a dynamic user interface 12. As shown, the AR system 10 includes a control system 14 that includes a processor 16, a memory 18, and a communication device 20. The AR system 10 also includes one or more devices that are configured to display AR imagery (e.g., AR images; virtual images) for visualization by a user. In some embodiments, the one or more devices include one or more wearable devices that are configured to be carried, held, and/or worn by the user. For example, as shown, the one or more wearable devices may include AR glasses 22 that are configured to be worn on a head of the user.

The AR glasses 22 may include a frame 24 that supports one or more displays 26 and an electronics package 28 (e.g., electronics system or assembly). The electronics package 28 may include a processor 30, a memory 32, and a communication device 34 that are part of an on-board control system 35. The electronics package 28 may also include one or more speakers 36, one or more microphones 38, one or more cameras 40, one or more face cameras 42, and/or one or more physiological sensors 44. Components of the electronics package 28 may be enclosed or supported within one or more housings. Further, the one or more displays 26 may be considered to be part of the electronics package 28.

The one or more displays 26 may refer to display surfaces that include features (e.g., circuitry, light emitters) that display the AR imagery, or the one or more displays 26 may refer to display surfaces that reflect light projected by projectors to display the AR imagery. Indeed, the one or more displays 26 may refer to display surfaces and any associated components (e.g., circuitry, light emitters, projectors, and/or any other associated components) that enable the display of the AR imagery for visualization by the user while the user wears the AR glasses 22. It should be appreciated that the one or more displays 26 may be transparent displays that enable the user to view a real-world environment (e.g., real objects in an environment surrounding the user) by looking through the one or more displays 26, and thus, the AR imagery presented on the one or more displays may appear to be overlaid onto the real-world environment from a perspective of the user while the user wears the AR glasses 22. That is, the user may view the AR imagery and the real-world environment together (e.g., simultaneously) while the user wears the AR glasses 22.

It should be appreciated that various alternatives are envisioned. For example, the AR glasses 22 may include an opaque display that displays the AR imagery and substantially real-time video streams of the real-world environment (e.g., obtained by the one or more cameras 40). As another example, the AR glasses 22 may include an opaque display that displays the AR imagery as part of an entirely virtual experience (e.g., without any representation of the real-world environment). Thus, the AR system 10 and the AR glasses 22 may incorporate or provide AR experiences in which the user is able to view the AR imagery and the real-world environment, AR experiences in which the user is able to view the AR imagery and the substantially real-time video streams of the real-world environment, VR experiences in which the user is able to view the AR imagery without the real-world environment, and/or mixed-reality experiences in which the user is able to alternate between the AR experiences and the VR experiences, for example.

The control system 14 may be communicatively coupled to the AR glasses 22, one or more additional devices 46 (e.g., wearable sensors, which may be integrated into a smart watch), and/or one or more databases 48 via a network 50 (e.g., one or more networks, such as short-range and/or long-range networks). In certain embodiments, the AR glasses 22 may be communicatively coupled to the one or more additional devices 46 and/or the one or more databases 48 via the network 50. In any case, the control system 14, the AR glasses, the one or more additional devices 46, and/or the one or more databases 48 may communicate to provide data, control signals, and so forth to facilitate techniques disclosed herein.

The processors 16, 30 may be configured to process instructions stored in the memory 18, 32 to operate the AR system 10. The processors 16, 30 may include hardware-based processors that each include one or more cores. The processors 16, 30 may include general purpose processors, special purpose processors, or both.

The memory 18, 32 may store information, including the instructions, within the AR system 10. In certain embodiments, the memory 18, 32 includes one or more computer-readable media. The memory 18, 32 may include any suitable number of volatile memory units and/or non-volatile memory units. The memory 18, 32 may include read-only memory, random access memory, or both. In certain embodiments, the memory 18, 32 may be configured to provide (e.g., persistent) mass storage for the AR system 10 and may include at least a portion of the one or more databases 48.

It should be appreciated that the memory 18, 32 may include one or more computer-readable storage media (CRSM). The CRSM may provide storage of the instructions (e.g., computer-readable instructions) describing data structures, processes, applications, programs, other modules, and/or other data for the operation of the AR system 10. In certain embodiments, the CRSM may include a data store that provides storage of the instructions and/or other information in a non-transitory format.

The communication devices 20, 34 may include transceiver devices configured to send and receive communications over the network 50 using any suitable network protocol. The network 50 may include public networks such as the Internet, private networks such as an institutional or personal intranet, or any combination of private and public networks. The network 50 may include any suitable type of wired or wireless network, including but not limited to local area networks (LANs), wide area networks (WANs), wireless WANs (WWANs), wireless LANs (WLANs), mobile communications networks (e.g., 3G, 4G, Edge, etc.), and so forth. In certain embodiments, the communications between computing devices (e.g., the control system 14 and the on-board control system 35) may be encrypted or otherwise secured. For example, the communications may employ one or more public or private cryptographic keys, ciphers, digital certificates, or other credentials supported by a security protocol.

The control system 14 and the on-board control system 35 may include one or more computing devices of any suitable type. The computing device(s) may include, but are not limited to: a personal computer, a smartphone, a tablet computer, a wearable computer, an implanted computer, a mobile gaming device, an electronic book reader, an automotive computer, a desktop computer, a laptop computer, a notebook computer, a game console, a home entertainment device, a network computer, a server computer, a mainframe computer, a distributed computing device (e.g., a cloud computing device), a microcomputer, a system on a chip (SoC), a system in a package (SiP), and so forth. Although examples herein may describe the computing device(s) as physical device(s), certain embodiments are not so limited. In some examples, the computing device(s) may include one or more of a virtual computing environment, a hypervisor, an emulation, or a virtual machine executing on one or more physical computing devices. In some examples, two or more computing devices may include a cluster, cloud, farm, or other grouping of multiple devices that coordinate operations to provide load balancing, failover support, parallel processing capabilities, shared processing resources, shared storage resources, shared networking capabilities, and/or other aspects. Accordingly, the control system 14 and the on-board control system 35 may be collectively referred to herein as a computing system (e.g. a processing system), and it should be appreciated that any of the processing operations described herein may be carried out by the control system 14, by the on-board control system 35, and/or distributed between the control system 14 and the on-board control system 35 in any manner to operate the AR system 10. Indeed, certain operations described herein as being performed by components of the control system 14 (e.g., the processor 16) may instead be performed by the on-board control system 35 (e.g., the processor 30), and vice versa.

In certain embodiments, the AR system 10 may include and/or utilize an insurance application (e.g., software application), which may be stored in the memory 32 of the on-board control system 35 of the AR glasses 22. In particular, the AR system 10 may utilize the insurance application to provide the dynamic user interface 12 for visualization by the user while the user wears the AR glasses 22. A software application (e.g., the insurance application; may also be referred to a program, software, script, or code) may be written in any appropriate form of programming language, including compiled or interpreted languages, and it may be deployed in any appropriate form, including as a standalone program or as a module, component, subroutine, or other unit suitable for use in a computing environment. The software application may be deployed to be executed on one computing device or on multiple computing devices that are located at one site or that are distributed across multiple sites and interconnected by the network 50.

In operation, the user may wear the AR glasses 22 and provide one or more inputs (e.g., initial inputs) to initiate an insurance process via the insurance application. For example, the user may provide an audio input to the one or more microphones 38, such as a spoken command (e.g., "I would like to renew my homeowner's insurance policy."). As another example, the user may provide a gesture input to the one or more cameras 40, such as to select a virtual icon for the insurance application shown in the AR imagery on the one or more displays 26. In response to receipt of the one or more inputs at the processor 30 of the on-board control system 35 of the AR glasses 22, the processor 30 may instruct the insurance application to open and/or may initiate communication with the control system 14 and/or the one or more databases 48 to access data about an insurance policy associated with the user. Then, in response to receipt of the data about the insurance policy associated with the user, the processor 30 may instruct display of information related to the insurance policy on the one or more displays 26. For example, the processor 30 may instruct display of a renewal date, a policy number, a policy type, and so forth.

In certain embodiments, the processing circuitry may utilize the one or more inputs (e.g., one or more audio inputs, such as spoken commands; one or more image inputs, such as one or more gesture inputs, real-world objects in the environment, gaze or eye movement, and/or facial expressions; and/or physiological parameter inputs) to determine and to provide certain relevant information related to the insurance policy on the one or more displays 26. For example, the processing system may process the one or more audio inputs to extract key words and/or phrases (e.g., "insurance," "renewal," "homeowner's"), and the processing system may select the information based on the key words and/or phrases (e.g., information related to renewal of the insurance policy).

Additionally or alternatively, the processing system may process the one or more image inputs to identify gesture inputs performed by the user (e.g., movement and/or location of hand(s) of the user in the environment), and the processing system may determine intended selections (e.g., virtual icons and/or menu items in the AR imagery) based on the gesture inputs. Then, the processing system may select the information based on the intended selections (e.g., renewal information for selections related to renewal of the insurance policy). Additionally or alternatively, the processing system may process the one or more image inputs to identify one or more real-world objects in the environment (e.g., structural features of a home, objects within or around the home). In particular, the processing system may process the one or more image inputs to identify the one or more real-world objects in the environment that may affect the insurance policy, such as construction materials, electronics, appliances, artwork, jewelry, damage, and so forth. The processing system may also determine characteristics (e.g., type, size, value) of the one or more real-world objects in the environment based on the one or more image inputs and/or external data (e.g., purchase data, insurance data, stored images) from the one or more databases 48. Then, the processing system may select the information based on the one or more real-world objects in the environment (e.g., a cost to add a particular real-world object during renewal of the insurance policy). It should be appreciated that the processing system may implement image processing techniques, machine learning algorithms, and/or any other suitable techniques to process the one or more inputs and/or to determine the information to provide on the one or more displays 26.

FIG. 1 includes an example of the dynamic user interface 12 with the relevant information on the one or more displays 26. The dynamic user interface 12 includes details for insurance renewal, which may be presented based on the one or more inputs (e.g., the spoken commands; the gesture inputs). Further, the dynamic user interface 12 includes a prompt related to coverage of a first object 60 as part of a renewal process, and the prompt may be presented based on detection of the first object 60 within a field of view of the one or more cameras 40. Thus, the user may view the first object 60 in the environment (e.g., the first object 60 is a real object viewable by user through the one or more displays 26 while the user wears the AR glasses 22) with the prompt related to the coverage of the first object 60 as the AR imagery overlaid onto the environment (e.g., the AR imagery is virtual imagery viewable by the user via the one or more displays 26 while the user wears the AR glasses 22). In this example, the prompt may guide the user to provide a response, such as via one or more audio inputs (e.g., spoken commands) for detection via the one or more microphones 38 and/or one or more gesture inputs (e.g., reaching out to a left side and performing a tapping gesture for "yes," or reaching out to a right side and performing the tapping gesture for "no") for detection via the one or more cameras 40.

It should be appreciated that variations are envisioned, such as variations in which the user may provide the one or more inputs and/or the response via gaze direction (e.g., eye gaze determined to align with or focus on the first object 60 for a threshold time causes the prompt related to the coverage of the first object 60; looking to the left side for "yes," and looking to the right side for "no") for detection via the one or more face cameras 42 that are positioned to capture one or more images of a face of the user and/or one or both eyes of the user. In any case, the user may provide the one or more inputs to cause selection and presentation of the information on the one or more displays 26, as well as to interact with the information on the one or more displays 26 to carry out an interactive process, such as for the insurance renewal. Thus, the AR system 10 may provide the dynamic user interface 12 that changes content based on the one or more inputs (e.g., as the user moves to place other real objects in the environment within the field of view of the one or more cameras 40, as the user provides other spoken commands, and so forth).

In some embodiments, the AR system 10 may determine a sentiment (e.g., characteristic; emotional and/or physiological response) of the user based on the one or more inputs. Then, the AR system 10 may make changes to a format (e.g., the content and/or a layout) of the relevant information on the one or more displays 26 based on the sentiment. In this way, the AR system 10 may provide the dynamic user interface 12 that changes the format based on both the interaction and/or the sentiment indicated by the one or more inputs. With this in mind, the AR system 10 may determine the sentiment of the user based on the audio inputs to the one or more microphones 38, the gesture inputs and/or other movements determined based on the image inputs obtained by the one or more cameras 40, eye gaze and/or facial expressions determined based on the image inputs obtained by the one or more face cameras 42, and/or the physiological parameters detected by the one or more physiological sensors 44 and/or detected by the one or more additional devices 46.

With reference to FIG. 1, the AR system 10 may determine a negative sentiment of the user (e.g., the user is frustrated, confused, stressed) based on the one or more inputs. For example, the audio inputs may include key words and/or phrases that correlate with the negative sentiment (e.g., "I do not understand"), the gesture inputs and/or other movements may indicate that the user is having difficulty selecting the virtual icons (e.g., "yes" or "no" to respond to the specific request; making hand movements, but do not correspond to selection within a threshold time, such as 2 minutes), the eye gaze indicates that the user is not focused on the first object 60 or the prompt, the facial expressions indicate the negative sentiment (e.g., frown, furrowed brows), and/or the physiological sensors indicate the negative sentiment (e.g., heart rate, respiration rate, blood pressure, muscle tension; elevated compared to baseline and/or in response to the presentation of the prompt).

Thus, the processing system may receive and process the one or more inputs in substantially real-time as the AR imagery is presented to the user via the one or more displays 26, and the processing system may identify any interactions with the AR imagery and/or may determine the negative sentiment of the user. In response to the negative sentiment of the user, the processing system may determine and implement one or more changes to the AR imagery. For example, the processing system may change the AR imagery, such as to re-format or change the information (e.g., content; amount and/or type; word choice; layout or arrangement; size and/or color of text, symbols, icons, and/or indicators; add and/or omit features, such as text; symbols; icons; indicators) in an attempt to change (e.g., improve) the negative sentiment of the user (e.g., to a neutral, positive, or less negative sentiment). It should be appreciated that the negative sentiment may include a neutral sentiment. Further, it should be appreciated that the processing system may be configured to identify a positive sentiment, a neutral sentiment, and a negative sentiment, as well as to determine and assign a score (e.g., on a numerical scale) to indicate a degree of positivity and/or negativity, for example.

As a more specific example, in FIG. 1, the dynamic user interface 12 may initially include the prompt related to whether to include the first object 60 for coverage by the insurance policy during the renewal process. If the processing system does not identify any negative sentiment of the user in response to display of the prompt and/or determines that the user successfully provides an appropriate input to the prompt (e.g., via spoken command, gesture input, eye gaze; within the threshold time), then the processing system may provide instructions to include the first object 60 for the coverage by the insurance policy during the renewal process and may also update the dynamic user interface 12, such as to include another prompt related to another object or to provide a confirmation, for example. However, if the processing system identifies the negative sentiment of the user in response to the prompt and/or determines that the user does not provide any appropriate input to the prompt (e.g., via spoken command, gesture input, eye gaze; within the threshold time), then the processing system may update the dynamic user interface 12, such as to include a symbol 62 (e.g., arrow) to draw attention to the first object 60 in an attempt to make the information provided on the one or more displays 26 easier to understand for the user and to improve the negative sentiment of the user, for example.

Figure 2:
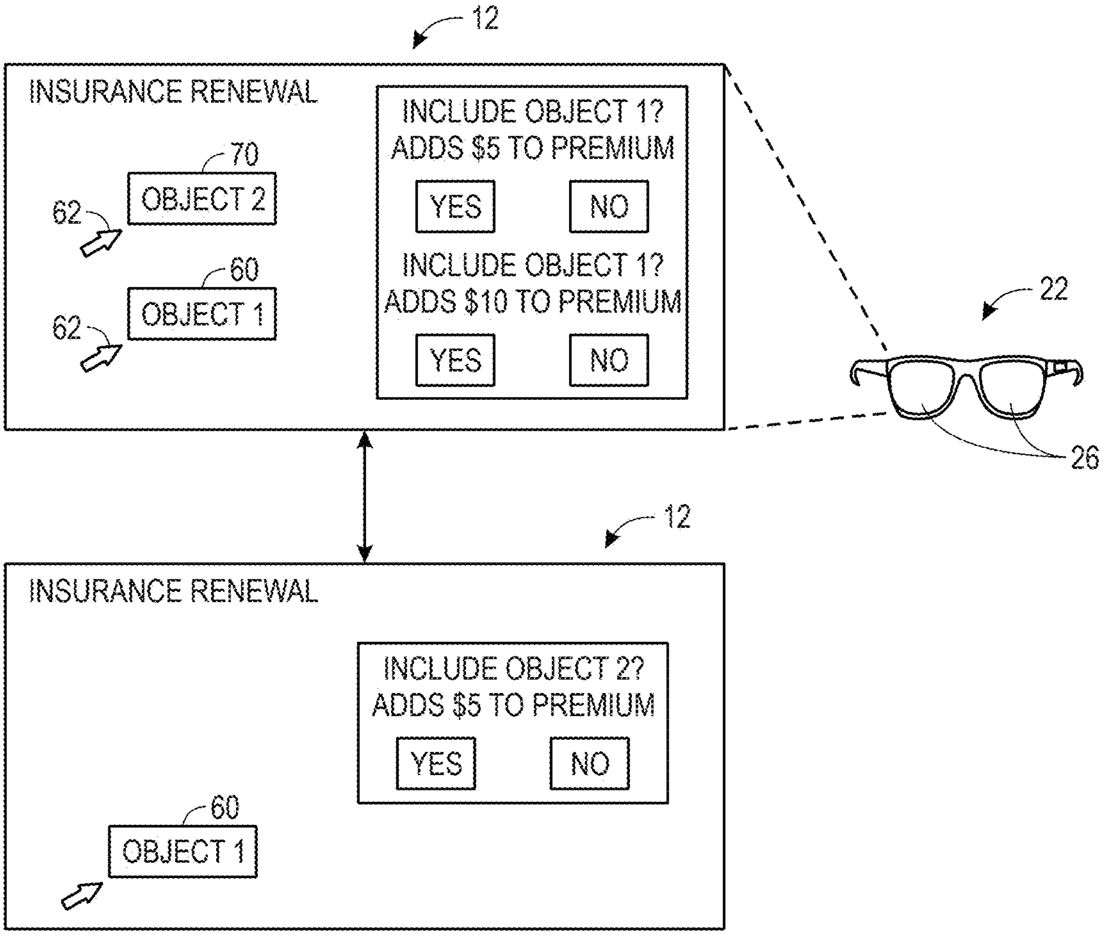
FIG. 2 is an example of a change to the dynamic user interface of FIG. 1, wherein the dynamic user interface presents one or more prompts related to renewal of an insurance policy, in accordance with an embodiment of the present disclosure.
Figure 3:
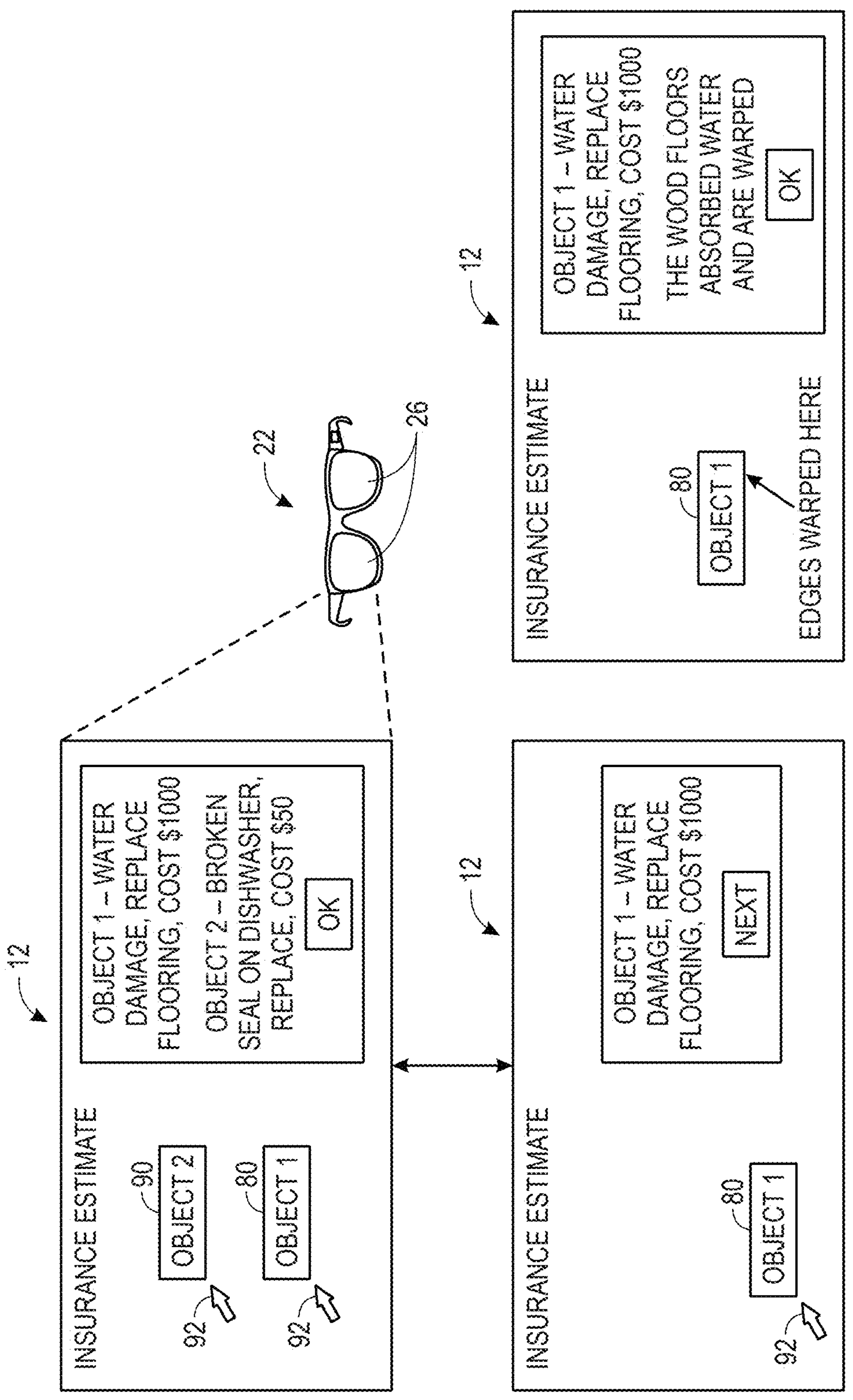
FIG. 3 is an example of a change to the dynamic user interface of FIG. 1, wherein the dynamic user interface presents one or more prompts related to an estimate for repair under an insurance policy, in accordance with an embodiment of the present disclosure.
Figure 4:
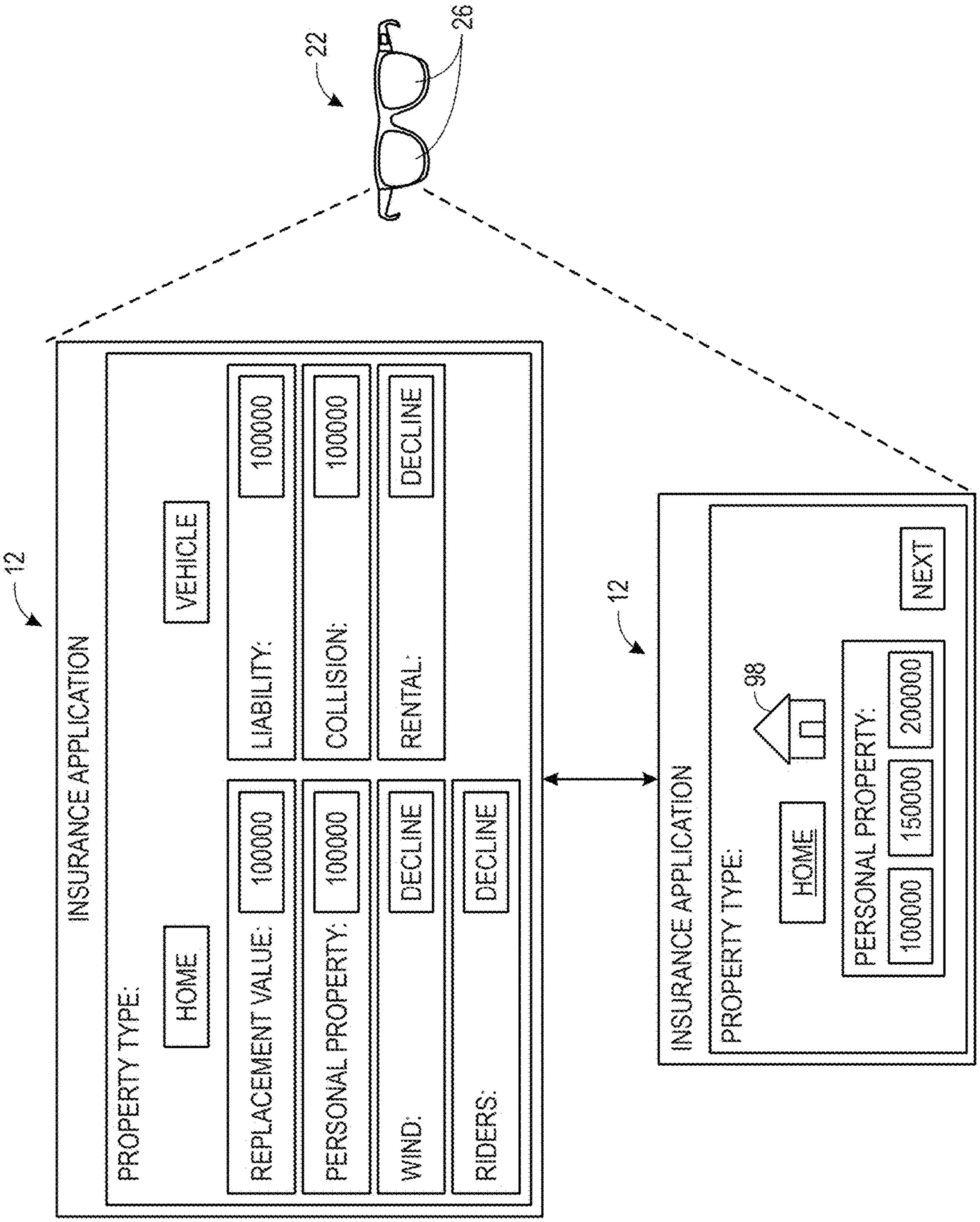
FIG. 4 is an example of a change to the dynamic user interface of FIG. 1, wherein the dynamic user interface presents one or more prompts related to an application for an insurance policy, in accordance with an embodiment of the present disclosure.

FIGS. 2-4 provide additional examples of changes to the dynamic user interface 12. In particular, FIG. 2 is an example of a change to the dynamic user interface 12, wherein the dynamic user interface 12 presents one or more prompts related to renewal of an insurance policy, in accordance with an embodiment of the present disclosure. As shown, the AR imagery is presented to the user via the one or more displays 26 of the AR glasses 22, and the AR imagery may initially include the prompt related to whether to include the first object 60 and a second object 70 for coverage by the insurance policy during the renewal process. The AR imagery may include the prompt in response to the first object 60 and the second object 70 being within the field of view of the one or more cameras 40 (FIG. 1) and/or in response to the eye gaze of the user being directed to the first object 60 and the second object 70 for a threshold time. Further, the AR imagery may include the prompt based on other inputs, including audio inputs (e.g., spoken commands).

However, if the processing system does not identify any negative sentiment of the user in response to display of the prompt and/or determines that the user successfully provides an appropriate input to the prompt (e.g., via spoken command, gesture input, eye gaze; within the threshold time), then the processing system may provide instructions to include the first object 60 and the second object 70 for the coverage by the insurance policy during the renewal process and may also update the dynamic user interface 12, such as to include another prompt related to another object or to provide a confirmation, for example. However, if the processing system identifies the negative sentiment of the user in response to the prompt and/or determines that the user does not provide any appropriate input to the prompt (e.g., via spoken command, gesture input, eye gaze; within the threshold time), then the processing system may update the dynamic user interface 12, such as to include symbols 62 (e.g., arrows) to draw attention to the first object 60 and the second object 70 in an attempt to make the information provided on the one or more displays 26 easier to understand for the user and to improve the negative sentiment of the user, for example. In some cases, if the processing system identifies the negative sentiment of the user continues after the update and/or determines that the user does not provide any appropriate input to the prompt after the update (e.g., within the threshold time), the processing system may update other features of the dynamic user interface 12, such as to color code the symbols 62 (e.g., one color for the symbol and text associated with the first object 60 and another color for the symbol and text associated with the second object 70) or to remove all information related to the second object 70 to allow the user to focus on only the first object 60.

The processing system may determine appropriate changes and updates to the dynamic user interface 12 based on the one or more inputs, which indicate details of the negative sentiment of the user. For example, the processing system may determine that the appropriate change includes color coding the symbols 62 in response to receipt of audio inputs with key words and/or phrases (e.g., "what is the first object?") related to confusion about which real object corresponds to the first object 60 (and corresponding insurance cost) and which real object corresponds to the second object 70 (and corresponding insurance cost) and/or based on eye gaze indicating that the eye gaze is transitioning between the first object 60 to the corresponding insurance cost for the second object 70 (e.g., mismatched object and insurance cost). In this way, the eye gaze may indicate that the user is having trouble reviewing or understanding a certain portion of the information or the one or more displays 26. It should also be appreciated that the eye gaze may be correlated to a change in one or more physiological parameters to determine that the user is having trouble reviewing or understanding a certain portion of the information or the one or more displays 26 (e.g., when the eye gaze transitions to and/or focuses on the certain portion is correlated to elevated physiological parameters indicative of stress). However, the processing system may determine that the appropriate change includes removal of all information related to the second object 70 in response to detected hand movements that are not precise enough to register as a selection of one of the virtual icons (e.g., "yes" or "no") and/or based on physiological parameters indicative of the negative sentiment (e.g., increase in heart rate; stress).

It should be appreciated that the processing system may request and/or obtain the one or more inputs periodically, continuously, and/or responsively (e.g., in response to the user opening the insurance application; in response to a change to the dynamic user interface 12), and the processing system may update the dynamic user interface 12 periodically, continuously, and/or responsively (e.g., in response to changes in the one or more inputs; in response to identifying the negative sentiment) to dynamically adapt the dynamic user interface 12 based on the one or more inputs to facilitate understanding and/or interactions with the user. Further, the processing system may make any of a variety of changes to the dynamic user interface 12. For example, the processing system may determine that the appropriate change includes adding more information (e.g., the first object 60, the second object 70, and a third object) in response to determining that the one or more inputs indicate that the user appears to be frustrated by reviewing each object one by one (e.g., spoken commands and/or elevated heart rate due to a slow renewal process) and that the user can precisely and efficiently interact with the dynamic user interface 12 (e.g., successful and efficient selection of the virtual icons), and so forth.

FIG. 3 is an example of a change to the dynamic user interface 12, wherein the dynamic user interface 12 presents one or more prompts related to an estimate for repair under an insurance policy, in accordance with an embodiment of the present disclosure. As shown, the AR imagery is presented to the user via the one or more displays 26 of the AR glasses 22, and the AR imagery may initially include a prompt related to an estimated repair cost associated with a first object 80 and a second object 90 under the insurance policy. The AR imagery may include the prompt in response to the first object 80 and the second object 90 being within the field of view of the one or more cameras 40 (FIG. 1) and/or in response to the eye gaze of the user being directed to the first object 80 and the second object 90 for a threshold time. Further, the AR imagery may include the prompt based on other inputs including audio inputs (e.g., spoken commands).

If the processing system does not identify any negative sentiment of the user in response to display of the prompt and/or determines that the user successfully provides an appropriate input to the prompt (e.g., via spoken command, gesture input, eye gaze; within the threshold time), then the processing system may provide instructions to proceed with repairs to the first object 80 and the second object 90 and may also update the dynamic user interface 12, such as to include another prompt(s) for another object(s) or to provide a confirmation, for example. However, if the processing system identifies the negative sentiment of the user in response to the prompt and/or determines that the user does not provide any appropriate input to the prompt (e.g., via spoken command, gesture input, eye gaze; within the threshold time), then the processing system may update the dynamic user interface 12, such as to include symbols 92 (e.g., arrows) to draw attention to the first object 80 and the second object 90 in an attempt to make the information provided on the one or more displays 26 easier to understand for the user and to improve the negative sentiment of the user, for example. In some cases, if the processing system identifies the negative sentiment of the user continues after the update and/or determines that the user does not provide any appropriate input to the prompt after the update, the processing system may update other features of the dynamic user interface 12, such as to color code the symbols 92, to remove all information related to the second object 90 to allow the user to focus on only the first object 80, or to provide additional information about the repairs.

As discussed herein, the processing system may determine appropriate changes and updates to the dynamic user interface 12 based on the one or more inputs, which indicate details of the negative sentiment of the user. For example, the processing system may determine that the appropriate change includes removal of all information related to the second object 90 and providing additional information about the repairs in response to detected hand movements that are not precise enough to register as a selection of one of the virtual icons (e.g., "yes" or "no"), based on eye gaze focusing on the first object 80, and/or based on physiological parameters indicative of the negative sentiment (e.g., increase in heart rate; stress).

It should be appreciated that the processing system may dynamically adapt the dynamic user interface 12 based on the one or more inputs to facilitate understanding and/or interactions with the user. Further, the processing system may make any of a variety of changes to the dynamic user interface 12. For example, the processing system may determine that the appropriate change includes adding more information (e.g., the first object 80, the second object 90, and a third object) in response to determining that the one or more inputs indicate that the user appears to be frustrated by reviewing each object one by one (e.g., spoken commands and/or elevated heart rate due to a slow renewal process) and that the user can precisely and efficiently interact with the dynamic user interface 12, and so forth.

FIG. 4 is an example of a change to the dynamic user interface 12, wherein the dynamic user interface 12 presents one or more prompts related to an application for an insurance policy, in accordance with an embodiment of the present disclosure. As shown, the AR imagery is presented to the user via the one or more displays 26 of the AR glasses 22, and the AR imagery may initially include a prompt related to insurance coverage associated with a first property and a second property. The AR imagery may include the prompt in response to receipt of the one or more inputs indicating a request to apply for the insurance coverage. In some cases, the AR imagery may be presented to fill a view of the user and/or to overlay an opaque or shaded background (e.g., to block a view of the environment). However, the processing system may still obtain and/or utilize the imagery within the field of view of the one or more cameras 40 (FIG. 1) to generate the prompt (e.g., asses the imagery that includes indications of the home, such as size and/or construction materials to provide options for the insurance coverage, such as value options for the parameters, including respective value options for replacement value, respective value options for personal property, and so forth).

If the processing system does not identify any negative sentiment of the user in response to display of the prompt and/or determines that the user successfully provides an appropriate input to the prompt (e.g., via spoken command, gesture input, eye gaze; within the threshold time), then the processing system may provide instructions to proceed with next steps for the insurance policy (e.g., review and/or generate) and may also update the dynamic user interface 12, such as to include another prompt or to provide a confirmation, for example. However, if the processing system identifies the negative sentiment of the user in response to the prompt and/or determines that the user does not provide any appropriate input to the prompt (e.g., via spoken command, gesture input, eye gaze; within the threshold time), then the processing system may update the dynamic user interface 12, such as to include symbols 98 (e.g., picture of a home) to improve aesthetics (e.g., increase visual interest) in an attempt to improve the negative sentiment of the user, for example. In some cases, if the processing system identifies the negative sentiment of the user continues after the update and/or determines that the user does not provide any appropriate input to the prompt after the update (e.g., within the threshold time), the processing system may update other features of the dynamic user interface 12, such as to remove information and to simplify the information in an attempt to make the information provided on the one or more displays 26 easier to understand for the user and to allow the user to focus on smaller pieces of the information related to the insurance policy at one time.

As discussed herein, the processing system may determine appropriate changes and updates to the dynamic user interface 12 based on the one or more inputs, which indicate details of the negative sentiment of the user. For example, the processing system may determine that the appropriate change includes removal of all information related to the second property and changing a format of the virtual icons (e.g., side by side instead of a drop down menu) in response to detected hand movements that are not precise enough to register as a selection of one of the virtual icons (e.g., in the drop down menu) and/or based on physiological parameters indicative of the negative sentiment (e.g., increase in heart rate; stress).

It should be appreciated that the processing system may dynamically adapt the dynamic user interface 12 based on the one or more inputs to facilitate understanding and/or interactions with the user. Further, the processing system may make any of a variety of changes to the dynamic user interface 12. For example, the processing system may determine that the appropriate change includes adding more information (e.g., the first property, the second property, and a third property; additional drop down menus and/or virtual icons) in response to determining that the one or more inputs indicate that the user appears to be frustrated by reviewing each property and/or parameter one by one (e.g., spoken commands and/or elevated heart rate due to a slow renewal process) and that the user can precisely and efficiently interact with the dynamic user interface 12, and so forth.

The AR system 10 may obtain (e.g., from the one or more databases 48 of FIG. 1) and/or determine (e.g., via machine learning; based on the one or more inputs, including the one or more physiological parameters, over time) preferences of the user. The AR system 10 may save the preferences of the user, update the preferences of the user as new data is received (e.g., over time), and/or implement the preferences to format the dynamic user interface 12. For example, if the one or more inputs indicate that the user experiences stress during presentation of a first format (e.g., drop-down menus or multiple policies) during a first AR experience (e.g., an insurance renewal process), then the AR system may block use or presentation of the first format during a remainder of the first AR experience and during subsequent AR experiences. Similarly, if the one or more inputs indicate that the user does not experience stress during presentation of a second format (e.g., side-by-side icons or single policy) during the first AR experience, then the AR system may enable use or presentation of the second format during the remainder of the first AR experience and during subsequent AR experiences. The AR system 10 may permanently remove or block certain formats in the way, or the AR system 10 may continue to adapt and adjust based on current inputs, which in certain cases may include reintroducing the first format (e.g., the user appears to have gained experience and/or demonstrates increased efficiency and/or improved sentiment over the subsequent AR experiences and/or negative sentiment over the subsequent AR experiences that indicates that the user is frustrated or bored, such as due to a slow renewal process provided via the first format).

Figure 5:
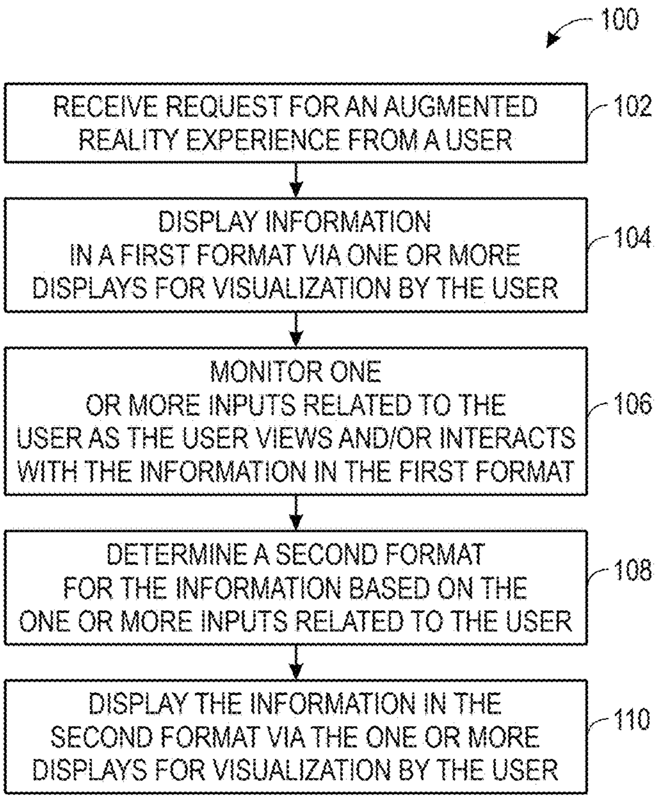
FIG. 5 is a flow diagram of a method of operating an augmented reality system to provide a dynamic user interface, in accordance with an embodiment of the present disclosure.

FIG. 5 is a flow diagram of a method 100 of operating an augmented reality (AR) system (e.g., the AR system of FIG. 1) to provide a dynamic user interface (e.g., the dynamic user interface 12 of FIGS. 1-4), in accordance with an embodiment of the present disclosure. The goal of the method 100 is to provide the dynamic user interface via the AR system to facilitate review of and/or interaction with information presented on the dynamic user interface. The information may relate to one or more insurance policies, and the dynamic user interface may dynamically change the information (e.g., format) to facilitate insurance renewal processes, insurance claims processes, insurance application processes, and/or any other insurance-related processes.

The following description of the method 100 is described as being performed by a processing system (e.g., the processor 16, the processor 30), but it should be noted that any suitable processor-based device or system may be specially programmed to perform any of the methods described herein. Moreover, although the following description of the method 100 is described as including certain steps performed in a particular order, it should be understood that the steps of the method 100 may be performed in any suitable order, that certain steps may be omitted, and/or that certain steps may be added.

In block 102, the method 100 may begin with receiving a request for an AR experience (e.g., AR interaction) from a user. The request for the AR experience may be made via one or more inputs at one or more devices of an AR system, such as at AR glasses of the AR system. For example, the user may provide a spoken command to initiate the AR experience, a keyed input to power on the AR glasses, and/or a gesture input to open an insurance application (e.g., software application) on the AR glasses.

In block 104, the method 100 may continue with the AR system displaying information in a first format via one or more displays of the one or more devices of the AR system, such as via the one or more displays of the AR glasses. The first format may be based on a default format (e.g., a first format provided to all users of the AR system) or an initial format that is specific to the user (e.g., based on preferences set by the user, such as during a registration process; based on prior interactions between the user and AR system, as the prior interactions may indicate interactive abilities and/or stress responses for certain formats, information levels, complexity, and so forth). For example, the first format may present options to add multiple objects to an insurance policy, as well as corresponding costs for each of the multiple objects. In response to receipt of the one or more inputs, the processing system may instruct the insurance application to open and/or may initiate communication with the one or more databases to access data about an insurance policy associated with the user.

In block 106, the method 100 may continue with monitoring one or more inputs related to the user as the user views and/or interacts with the information in the first format. The one or more inputs may include audio inputs (e.g., spoken commands) detected by one or more microphones, image inputs (e.g., indicative of features of an environment and/or gestures) detected by one or more cameras, image inputs (e.g., indicative of eye gaze and/or facial expressions) detected by one or more face cameras, and/or one or more physiological parameters (e.g., heart rate, respiration rate, blood pressure) detected by one or more physiological sensors, which may be supported on the AR glasses, for example. In some embodiments, the one or more inputs may additionally or alternatively include one or more physiological parameters detected by one or more additional devices (e.g., wearable sensors).

In block 108, the method 100 may continue with determining a second format for the information based on the one or more inputs related to the user as the user views and/or interacts with the information in the first format. In some embodiments, the AR system may determine a sentiment (e.g., characteristic; emotional and/or physiological response) of the user based on the one or more inputs related to the user. Then, the AR system may determine the second format (e.g., different than the first format) for the information based on the sentiment. In this way, the AR system may provide the dynamic user interface that adapts to the user based on the sentiment indicated by the one or more inputs related to the user.

For example, the AR system may identify a negative sentiment of the user (e.g., the user is frustrated, confused, stressed) based on the one or more inputs. For example, the audio inputs may include key words and/or phrases that correlate with the negative sentiment, the gesture inputs and/or other movements may indicate that the user is having difficulty selecting the virtual icons, the eye gaze may indicate that the user is not focused on appropriate features of the AR imagery, the facial expressions may indicate the negative sentiment, and/or the physiological sensors may indicate the negative sentiment. In this way, the AR system may receive and process the one or more inputs in substantially real-time as the AR imagery is presented to the user via the one or more displays, and the AR system may identify any interactions with the AR imagery and/or may determine the negative sentiment of the user.

In block 110, the method 100 may continue with the AR system displaying the information in the second format via the one or more displays of the one or more devices of the AR system, such as via the one or more displays of the AR glasses. For example, the processing circuitry may change the AR imagery, such as to re-format or change the information (e.g., content; amount and/or type; word choice; layout or arrangement; size and/or color of text, symbols, icons, and/or indicators; add and/or omit features, such as text; symbols; icons; indicators) in an attempt to change (e.g., improve) the negative sentiment of the user (e.g., to a neutral, positive, or less negative sentiment). In this way, the AR system may present the information in a dynamic manner that facilitates the interactions by the user to complete the insurance processes.

Figure 6:
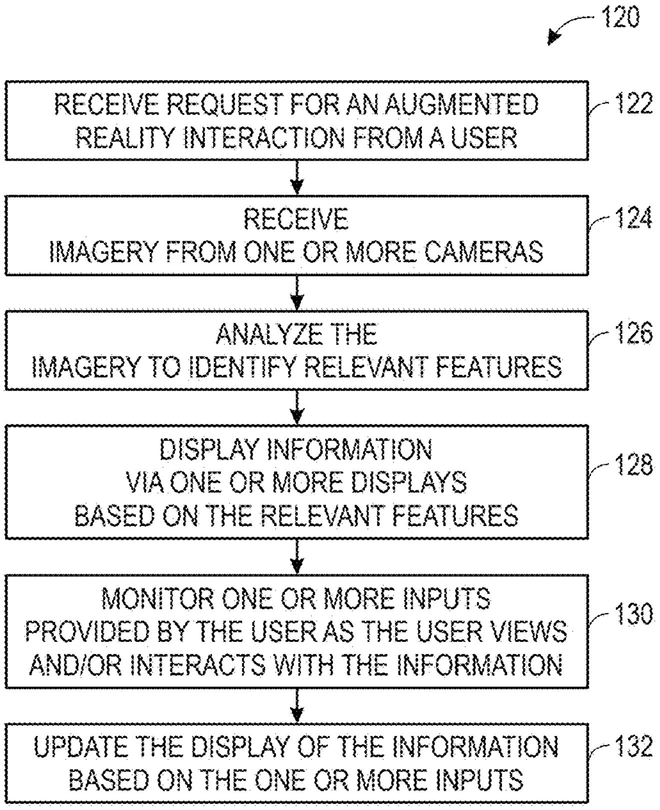
FIG. 6 is a flow diagram of a method of operating an augmented reality system to provide a dynamic user interface based on imagery captured by one or more cameras, in accordance with an embodiment of the present disclosure.

FIG. 6 is a flow diagram of a method 120 of operating an augmented reality (AR) system (e.g., the AR system of FIG. 1) to provide a dynamic user interface (e.g., the dynamic user interface 12 of FIGS. 1-4), in accordance with an embodiment of the present disclosure. The goal of the method 120 is to provide the dynamic user interface via the AR system to facilitate presentation of information that is relevant to the user and/or to facilitate interaction with the information. The information may relate to one or more insurance policies, and the dynamic user interface may dynamically change the information (e.g., content and/or format) to facilitate insurance renewal processes, insurance claims processes, insurance application processes, and/or any other insurance-related processes.

The following description of the method 120 is described as being performed by a processing system (e.g., the processor 16, the processor 30), but it should be noted that any suitable processor-based device or system may be specially programmed to perform any of the methods described herein. Moreover, although the following description of the method 120 is described as including certain steps performed in a particular order, it should be understood that the steps of the method 120 may be performed in any suitable order, that certain steps may be omitted, and/or that certain steps may be added.

In block 122, the method 120 may begin with receiving a request for an AR experience (e.g., AR interaction) from a user. The request for the AR experience may be made via one or more inputs at one or more devices of an AR system, such as at AR glasses of the AR system. For example, the user may provide a spoken command to initiate the AR experience, a keyed input to power on the AR glasses, and/or a gesture input to open an insurance application (e.g., software application) on the AR glasses.

In block 124, the method 120 may continue with receipt of imagery from one or more cameras, which may be supported by the AR glasses. The imagery may include one or more real-world objects that are positioned within a field of view of the one or more cameras.

In block 126, the method 120 may continue with image processing techniques to identify features of the imagery that are relevant to an insurance policy and/or the request for the AR experiences (e.g., identify objects of value in the imagery when the request relates to an insurance renewal or insurance application; identify signs of damage in the imagery when the request relates to an insurance claim). The image processing techniques may include template matching (e.g., matching the features in the imagery to stored object images in one or more databases), machine learning, and/or any other suitable image processing techniques. It should be appreciated that the method 120 may also include assessing audio inputs (e.g., spoken commands that describe objects to be assessed for coverage and/or damage). Further, the AR system may access data about an insurance policy associated with the user from the one or more databases.

In block 128, the method 120 may continue with the AR system displaying information via one or more displays of the one or more devices of the AR system, such as via the one or more displays of the AR glasses. For example, the information may include options to add the one or more real objects to the insurance policy, as well as corresponding costs.

In block 130, the method 120 may continue with monitoring the one or more inputs provided by user as the user views and/or interacts with the information. The one or more inputs may include audio inputs (e.g., spoken commands) detected by one or more microphones and/or imagery indicative of features of an environment and/or gesture inputs detected by one or more cameras.

In block 132, the method 120 may continue with updating the dynamic user interface based on the one or more inputs provided by the user. For example, the AR system may update the dynamic user interface in response to the audio inputs indicative of a selection of a virtual icon (e.g., "yes, I would like to cover a first object" or "are there other options for including the second object in the insurance policy?"). In this way, the AR system may provide a responsive AR experience that responds to the spoken commands of the user in substantially real-time to guide the user through the insurance processes.

As another example, the AR system may update the dynamic user interface in response to the image inputs indicating the gesture inputs made by the user indicative of the selection of the virtual icon (e.g., wave arm to the left for "yes" and wave arm to the right for "no"). In this way, the AR system may provide a responsive AR experience that responds to the gesture inputs of the user in substantially real-time to guide the user through the insurance processes. As another example, the AR system may update the dynamic user interface in response to the image inputs including different real objects. Thus, if the user turns their head while wearing the AR glasses, such that the first object is no longer in the field of the view of the one or more cameras (e.g., the one or more cameras may capture a space forward of the user and may generally capture and/or overlap with a field of view of the user) and a new object is now in the field of view of the one or more cameras, the AR system may update the dynamic user interface to reflect current objects being viewed by the user. Additionally or alternatively, the AR system may update the dynamic user interface in response to the image inputs indicating eye gaze of the user with focus on different real world objects (e.g., as focus lands on a particular real world object, such as for the threshold time, present information relevant to the particular real world object). In this way, the AR system may provide a responsive AR experience that responds to changes in the view of the user in substantially real-time to guide the user through the insurance processes.

As noted herein, the AR system may update the dynamic user interface based on the one or more inputs indicative of interactions with the AR imagery and/or the one or more inputs indicative of the sentiment of the user. Accordingly, aspects of the method 100 and the method 120 may be combined in any suitable manner to provide the dynamic user interface. Further, while examples provided herein relate to providing the AR imagery to create the dynamic user interface with information related to insurance policies to facilitate insurance processes, it should be appreciated that the AR system may be utilized to provide the AR imagery to create the dynamic user interface with information related to financial policies, financial accounts, financial records, medical policies, medical accounts, medical records, employment policies, school policies, school records, travel policies, travel itineraries, purchase policies, return policies, and so forth. Further, the AR system may be utilized to provide the AR imagery to facilitate financial processes, medical processes, employment processes, school processes, travel processes, shopping processes, and so forth. Indeed, the AR system and the techniques disclosed herein to provide the AR imagery to create the dynamic user interface (e.g., automatically and dynamically updated based on the one or more inputs, including the one or more physiological parameters) may be utilized in any of a variety of contexts and for any of a variety of purposes.

While only certain features of the disclosure have been illustrated and described herein, many modifications and changes will occur to those skilled in the art. It is, therefore, to be understood that the appended claims are intended to cover all such modifications and changes as fall within the true spirit of the disclosure. It should be appreciated that any features shown or described with reference to FIGS. 1-6 may be combined in any suitable manner.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for (perform)ing (a function) . . . " or "step for (perform)ing (a function) . . . ", it is intended that such elements are to be interpreted under 35 U.S.C. 112(f). However, for any claims containing elements designated in any other manner, it is intended that such elements are not to be interpreted under 35 U.S.C. 112(f).

The invention claimed is:

1. An augmented reality (AR) system, comprising:

a processing system comprising one or more processors; and memory storing instructions executable by the processing system to cause the processing system to:

instruct display of information in a first format via a display of an AR device;

monitor one or more physiological parameters of a user as the user views the information in the first format via the display of the AR device; and in response to the one or more physiological parameters of the user indicating a negative sentiment of the user as the user views the information in the first format via the display of the AR device, instruct display of the information in a second format via the display of the AR device, wherein the second format comprises a reduced amount of text, menu options, or both, relative to the first format so as to display the information in a simplified manner relative to the first format.

2. The AR system of claim 1, wherein the one or more physiological parameters comprise heart rate, respiration rate, blood pressure, or any combination thereof.

3. The AR system of claim 1, wherein the AR device comprises AR glasses configured to be worn on a head of the user.

4. The AR system of claim 3, wherein the display is a transparent display that enables the user to view a real-world environment through the display.

5. The AR system of claim 1, wherein the instructions are executable by the processing system to cause the processing system to:

receive image data from one or more cameras of the AR device;

process the image data to identify a first object and a second object in a real-world environment;

access data associated with the first object and the second object from one or more databases; and instruct display of the information in the first format to include the data associated with the first object and the second object.

6. The AR system of claim 5, wherein the instructions are executable by the processing system to cause the processing system to instruct display of the information in the second format to include the data associated with the first object and not the second object.

7. The AR system of claim 1, wherein the second format comprises the reduced amount of text relative to the first format so as to display the information in the simplified manner relative to the first format.

8. The AR system of claim 1, wherein the second format comprises the reduced amount of menu options, and the reduced amount of menu options comprises fewer virtual inputs that are selectable via gesture inputs from the user relative to the first format so as to display the information in the simplified manner relative to the first format.

9. The AR system of claim 1, wherein the second format comprises additional color indicators relative to the first format.

10. The AR system of claim 1, wherein the instructions are executable by the processing system to cause the processing system to:

monitor eye gaze of the user as the user views the information in the first format via the display of the AR device; and in response to the eye gaze of the user indicating focus on the information in the first format without a selection of a virtual input within a threshold time, instruct display of the information in a second format via the display of the AR device.

11. The AR system of claim 1, wherein the information relates to an insurance policy, and the instructions are executable by the processing system to cause the processing system to receive inputs from the user to enable the user to complete an insurance renewal process, an insurance claim process, an insurance application process, or any combination thereof.

12. An augmented reality (AR) system, comprising:

a processing system comprising one or more processors; and memory storing instructions executable by the processing system to cause the processing system to:

receive a request from a user to initiate an AR experience via an AR device;

access data associated with the user from one or more databases;

instruct display of information via a display of the AR device to present at least some of the data associated with the user;

receive one or more inputs from the user as the user views the information via the display of the AR device; and based on the one or more inputs from the user, modify a format in which the information is displayed via the display of the AR device by decreasing an amount of text, menu options, or both, used to display the information.

13. The AR system of claim 12, wherein the one or more inputs comprise eye gaze, heart rate, respiration rate, blood pressure, or any combination thereof.

14. The AR system of claim 12, wherein the instructions are executable by the processing system to cause the processing system to, in response to the one or more inputs from the user indicating a negative sentiment of the user as the user views the information via the display of the AR device, modify the format in which the information is displayed via the display of the AR device by decreasing the amount of text, menu options, or both, used to display the information.

15. The AR system of claim 14, wherein the instructions are executable by the processing system to cause the processing system to select the format based on prior interactions between the user and the AR system.

16. The AR system of claim 12, wherein the instructions are executable by the processing system to cause the processing system to:

receive image data from one or more cameras of the AR device;

process the image data to identify a first object in a real-world environment;

access the data associated with the first object and an insurance policy of the user from one or more databases; and instruct display of the information via the display of the AR device to enable the user to view the first object in the real-world environment through the display and the information overlaid onto the real-world environment via the display.

17. A method of operating an augmented reality (AR) device, the method comprising:

instructing, using a processing system, display of information in a first format via a display of an AR device;

receiving, from one or more sensors and at the processing system, one or more physiological parameters of a user as the user views the information in the first format via the display of the AR device; and instructing, using the processing system, display of the information in a second format via the display of the AR device in response to the one or more physiological parameters of the user indicating a negative sentiment of the user as the user views the information in the first format via the display of the AR device, wherein the second format comprises a reduced amount of text, menu options, or both, relative to the first format so as to display the information in a simplified manner relative to the first format.

18. The method of claim 17, wherein the one or more physiological parameters comprise heart rate, respiration rate, blood pressure, or any combination thereof.

19. The method of claim 17, wherein the second format is different relative to the first format with respect to content, word choice, number of words, layout, or any combination thereof.

20. The method of claim 17, comprising selecting the first format based on prior interactions between the user and the AR device.

* * * * *